US006494897B2

(12) United States Patent
Sterman et al.

(10) Patent No.: US 6,494,897 B2
(45) Date of Patent: Dec. 17, 2002

(54) METHODS AND SYSTEMS FOR PERFORMING THORACOSCOPIC CARDIAC BYPASS AND OTHER PROCEDURES

(75) Inventors: Wesley D. Sterman, San Francisco, CA (US); Lawrence C. Siegel, Hillsborough, CA (US); Patricia E. Curtis, Hillsborough, CA (US); John H. Stevens, Palo Alto, CA (US); Timothy R. MacHold, Moss Beach, CA (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/945,867

(22) Filed: Sep. 4, 2001

(65) Prior Publication Data
US 2002/0023653 A1 Feb. 28, 2002

Related U.S. Application Data

(62) Division of application No. 09/411,503, filed on Oct. 4, 1999, now Pat. No. 6,311,693, which is a continuation of application No. 08/559,613, filed on Mar. 12, 1996, now Pat. No. 5,961,481, which is a division of application No. 08/749,384, filed on Nov. 6, 1996, now Pat. No. 5,855,210, which is a continuation of application No. 08/376,330, filed on Jan. 20, 1995, now abandoned, which is a division of application No. 08/023,778, filed on Feb. 22, 1993, now Pat. No. 5,452,733.

(51) Int. Cl.⁷ .............................................. A61M 29/00
(52) U.S. Cl. ....................................................... 606/213
(58) Field of Search .......................... 128/898; 606/213, 606/215, 185, 151, 153, 191; 604/164, 174, 93; 600/204, 207, 208

(56) References Cited

U.S. PATENT DOCUMENTS

| 4,173,981 A | 11/1979 | Mortensen |
| 4,318,401 A | 3/1982 | Zimmerman |
| 4,808,163 A | 2/1989 | Laub |
| 5,011,469 A | 4/1991 | Buckberg et al. |
| 5,104,393 A | 4/1992 | Isner et al. |
| 5,109,859 A | 5/1992 | Jenkins |
| 5,167,628 A | 12/1992 | Boyles |
| 5,188,619 A | 2/1993 | Myers |
| 5,203,776 A | 4/1993 | Durfee |
| 5,211,683 A | 5/1993 | Maginot |
| 5,250,038 A | 10/1993 | Melker et al. |
| 5,304,220 A | 4/1994 | Maginot |
| 5,308,320 A | 5/1994 | Safar et al. |
| 5,312,344 A | 5/1994 | Grinfeld et al. |
| 5,339,800 A | 8/1994 | Witta et al. |
| 5,433,700 A | 7/1995 | Peters |
| 5,456,712 A | 10/1995 | Maginot |
| RE35,352 E | 10/1996 | Peters |
| 5,584,803 A | 12/1996 | Stevens et al. |

OTHER PUBLICATIONS

Landreneau, et al Ann. Thorac Surg 54:800–807; 1992.*

Mack, et al., "Present Role of Thoracoscopy in the Diagnosis and Treatment of Diseases of the Chest", Ann Thorac Surg. 54:403–9 (1992).

Landreneau et al. Video–Assisted Thoracic Surgery: Basic Technical Concepts and Intercostal Approach Strategies, Ann Thorac Surg, 54:800–807.

Primary Examiner—David J Isabella

(57) ABSTRACT

A method for closed-chest cardiac surgical intervention relies on viewing the cardiac region through a thoracoscope or other viewing scope and endovascularly partitioning the patient's arterial system at a location within the ascending aorta. The cardiopulmonary bypass and cardioplegia can be induced, and a variety of surgical procedures performed on the stopped heart using percutaneously introduced tools. The method of the present invention will be particularly suitable for forming coronary artery bypass grafts, where an arterial blood source is created using least invasive surgical techniques, and the arterial source is connected to a target location within a coronary artery while the patient is under cardiopulmonary bypass and cardioplegia.

1 Claim, 9 Drawing Sheets

OTHER PUBLICATIONS

Medi–tech.RTM., Instructions for Use, Occlusion Balloon Catheters Rev. Mar. 1991, p. 1–7.

Buckberg, G.D. "Strategies and Logic of Cardioplegic Delivery to Prevent, Avoid, and Reverse Ischemic and Reperfusion Damage," J Thorac Cardio Vasc Surg, 93:127–199 (1987).

Yamaguchi, A. "A Case of a Reoperation Using a Balloon Catheter with Blocked Pars Ascendes Aortae," Kyobu Geka, Oct., 42(11):961–964 (1991).

Peters, W.S. "The Promise of Cardioscopic Surgery," Austral As J Cardiac Thorac Surg, 2(3):152–154 (1993).

Raxi, D.M. "The Challenge of Calcific Aortitis," J Cardiac Thorac Surg, 8:102–107 (1993).

Ogawa, K. "Aortic Arch Reconstruction with Aortic Cross–Clamping Using Separate Extracorporeal Circulation," J Jpn Assn Thorac Surg, 2185–2190 (1993).

Gundry et al. "A Comparison of Retrograde Cardioplegia Versus Antegrade Cardioplegia in the Presence of Coronary Artery Obstruction," Ann Thorac Surg, 38(2):124–127 (1984).

Lust et al. "Improved Protection of Chronically Inflow–Limited Myocardium with Retrograde Coronary Sinus Cardioplegia," Circulation III, 78(5):217–223 (1988).

Crooke et al. "Biventricular Distribution of Cold Blood Cardioplegic Solution Administered by Different Retrograde Techniques," J Cardiac Thorac Surg, 102(4):631–636 (1991).

Sabiston, D.C. Textbook of Surgery, 10th Ed. 2021–2023, 2114–2121, (1972).

Ishizaka, Myocardial Protection by Retrograde Cardiac Perfusion with Cold Modified Krebs Solution Through Coronary Sinus During Complete Ischemic Arrest for 120 min, J Jpn. Assn. Thorac. Surg, 25(12):1592–1601 (1977).

Takahashi, M., Retrograde Coronary Sinus Perfusion for Myocardial Protection in Aortic Valve Surgery, J Jpn Assn Thorac Surg, 30(3):306–318 (1982).

Cosgrove, D.M. "Management of Calcified Aorta: An Alternative Method of Occlusion" Ann Thorac Surg, 36:718–719 (1983).

Foster and Threlkel "Proximal Control of Aorta with a Balloon Catheter", Surg Gynecology & Obstetrics, 693–694 (1971).

Erath and Stoney, "Balloon Catheter Occlusion of the Ascending Aorta" Ann Thorac Surg, 35:560–561 (1983).

Sakaguchi et al. "Aortic Valve Replacement and Coronary Artery Bypass" J Jap Assoc for Thorac Surg, 41(6):1063–1068 (1993).

* cited by examiner

METHODS AND SYSTEMS FOR PERFORMING THORACOSCOPIC CARDIAC BYPASS AND OTHER PROCEDURES

CROSS REFERENCE TO RELATED APPLICATIONS

This application is a division of Ser. No. 09/411,503, filed Oct. 4, 1999, now issued as U.S. Pat. No. 6,311,693, which is a continuation of application Ser. No. 08/559,613, filed Mar. 12, 1996, now issued as U.S. Pat. No. 5,961,481, which is a division of application Ser. No 08/749,384, filed Nov. 6, 1996, now issued as U.S. Pat. No. 5,855,210, which is a continuation of application Ser. No. 08/376,330, filed Jan. 20, 1995, now abandoned, which is a division of Ser. No. 08/023,778, filed Feb. 22, 1993, now issued as U.S. Pat. No. 5,452,733. The complete disclosures of these applications are hereby incorporated herein by reference for all purposes.

BACKGROUND OF THE INVENTION

1. Field of the Invention

The present invention relates generally to thoracoscopic methods for performing cardiac procedures. More particularly, the present invention relates to thoracoscopic methods for performing procedures externally on or internally within the heart while the patient's chest is unopened, the patient's heart is stopped, and the patient is supported by cardiopulmonary bypass.

Coronary artery disease remains the leading cause of morbidity and mortality in Western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of approaches have been developed for treating coronary artery disease. In less severe cases, it is often sufficient to treat the symptoms with pharmaceuticals and lifestyle modification to lessen the underlying causes of disease. In more severe cases, the coronary blockage(s) can often be treated endovascularly using techniques such as balloon angioplasty, atherectomy, laser ablation, stents, hot tip probes, and the like.

In cases where pharmaceutical treatment and/or endovascular approaches have failed or are likely to fail, it is often necessary to perform a coronary artery bypass graft procedure using open surgical techniques. Such techniques require that the patient's sternum be opened and the chest be spread apart to provide access to the heart. A source of arterial blood is then connected to a coronary artery downstream from an occlusion while the patient is maintained under cardioplegia and is supported by cardiopulmonary bypass. The source of blood is often the left or right internal mammary artery, and the target coronary artery can be the left anterior descending artery or any other coronary artery which might be narrowed or occluded.

While very effective in many cases, the use of open surgery to perform coronary artery bypass grafting is highly traumatic to the patient. The procedure requires immediate postoperative care in an intensive care unit, a total period of hospitalization of seven to ten days, and a recovery period that can be as long as six to eight weeks.

It would therefore be desirable to provide other, less traumatic methods and techniques for performing coronary artery bypass grafting. It would be particularly desirable if such techniques did not require opening of the patient's sternum, and might be even more desirable if such techniques could be performed using thoracoscopic methods. Such thoracoscopic methods could decrease morbidity and mortality, cost, and recovery time when compared to conventional open surgical coronary bypass procedures. In addition, such methods could be even more efficacious than open-surgical bypass procedures.

2. Description of the Background Art

Conventional thoracoscopic techniques are described in Landreneau et al. (1992) Ann. Thorac. Surg. 54:800–807. Conventional open surgical procedures for performing coronary artery bypass grafting are described in Kirklin and Barratt Boyes, *Cardiac Surgery*, John Wiley & Sons, Inc. New York, 1993 (2nd Ed.). Copending application Ser. No. 07/730,599, assigned to the assignee of the present application, describes a catheter which is insertable into a patient's arterial system and includes a distal balloon which can be expanded to occlude the ascending aorta. The coronary ostia remain unblocked so that the heart and proximal ascending aorta may be isolated while the patient is on cardiopulmonary bypass. This catheter is particularly intended to be used in heart valve replacement procedures.

SUMMARY OF THE INVENTION

According to the present invention, a method for closed-chest cardiac surgical intervention relies on viewing the region of the heart through a percutaneously positioned viewing scope, such as a thoracoscope. The patient's arterial system will be partitioned during such interventional procedures at a location within the ascending aorta between the brachiocephalic artery and the coronary ostia. In a preferred embodiment, such partitioning is achieved by endovascularly advancing the distal end of a catheter to the desired location with the ascending aorta and expanding a blocking element on the catheter at said location to inhibit the flow of blood and other fluids past said location. Such partitioning facilitates isolation of the heart, and in particular permits the heart to be stopped while the patient is supported by cardiopulmonary bypass. Once the patient's heart is stopped, a variety of surgical procedures can be performed using percutaneously introduced instruments in a minimally invasive fashion.

The methods of the present invention will be particularly useful for forming coronary artery bypass grafts in a patient suffering from coronary artery disease. The methods will be performed while the treating physician views the region of the heart through the viewing scope, with initial portions of the procedures being performed while normal heart function is maintained. As a first step, the physician will prepare an arterial blood source, typically by harvesting an internal mammary artery or other suitable artery. Conveniently, the lung beneath the internal mammary artery will be collapsed while the other lung remains ventilated. After the arterial blood source is prepared, cardiopulmonary bypass will be established, the patient's arterial system will be partitioned, and the heart stopped, typically by introducing cardioplegic fluid to the isolated heart. A target location on the coronary artery will then be prepared to receive attachment of the arterial blood source, typically by forming an incision at a location downstream from a narrowed region in the artery. The arterial blood source can be connected to the coronary artery by various conventional anastomotic techniques, such as suturing.

The methods of the present invention provide a minimally-invasive approach for forming coronary artery bypass grafts with an efficacy equal to or greater than conventional open surgical bypass techniques. The methods of the present invention can be adapted to create anastomoses of a variety and type similar to those created by open surgical techniques, while greatly reducing patient trauma since there is no need to perform a sternotomy. Moreover, the preferred use of an endovascular catheter to partition the aorta and isolate the heart offers a substantial advantage over open surgical techniques where external clamps are placed on the aorta. External clamps can damage the aorta and may frequently cause the release of emboli from the aortic lumen. Additionally, since the sternum does not need to heal after the procedure, both internal mammary arteries can frequently be used in a single procedure to provide multiple bypass routes. Heretofore, one internal mammary artery was often left in place to provide blood flow to promote healing of the sternum in many open-surgical procedures.

BRIEF DESCRIPTION OF THE DRAWINGS

FIG. 6 further illustrates the connection of a cardiopulmonary bypass system to the patient, as well as the optional placement of a retrograde cardioplegia catheter.

DESCRIPTION OF SPECIFIC EMBODIMENTS

The methods of the present invention are suitable for performing a variety of surgical cardiac procedures where the heart will be stopped and the patient supported by cardiopulmonary bypass. The procedures will be minimally invasive and be performed using surgical instruments introduced through a plurality of trocar sheaths placed through the patient's chest. A viewing scope, such as a thoracoscope, will be placed through at least one of the trocar sheaths, and selected surgical instruments will be placed through others of the trocar sheaths and their manipulation viewed by the treating physician using the viewing scope. The methods of the present invention are particularly suitable for forming coronary artery bypass grafts, but will also find use in a variety of other procedures, such as mitral valve repair; mitral valve replacement; thrombectomy of the pulmonary artery, left atrium, or left ventricle; removal of atrial myxoma; atrial or ventricular septal defect closure; patent foramen ovale closure; tricuspid valve annuloplasty; tricuspid valve replacement; ventricular aneurysmectomy; thermal and mechanical cardiac ablation procedures to correct arrhythmias; and the like.

The method of the present invention for performing a coronary artery bypass graft will now be described in detail. The patient undergoing the procedure is prepared in a conventional manner for cardiac surgery. Additionally, both groins are prepared to permit access to the femoral arteries and veins for cardiopulmonary bypass and introduction of the aortic occlusion catheter, as described in more detail hereinafter. The abdomen will also be prepared in case it is necessary to obtain access to an abdominal artery (for example, the gastroepiploic artery) for use in the bypass procedure. The patient is placed under general anesthesia, and a double-lumen endobronchial tube is inserted for selective ventilation or deflation of either lung.

Figure 1:
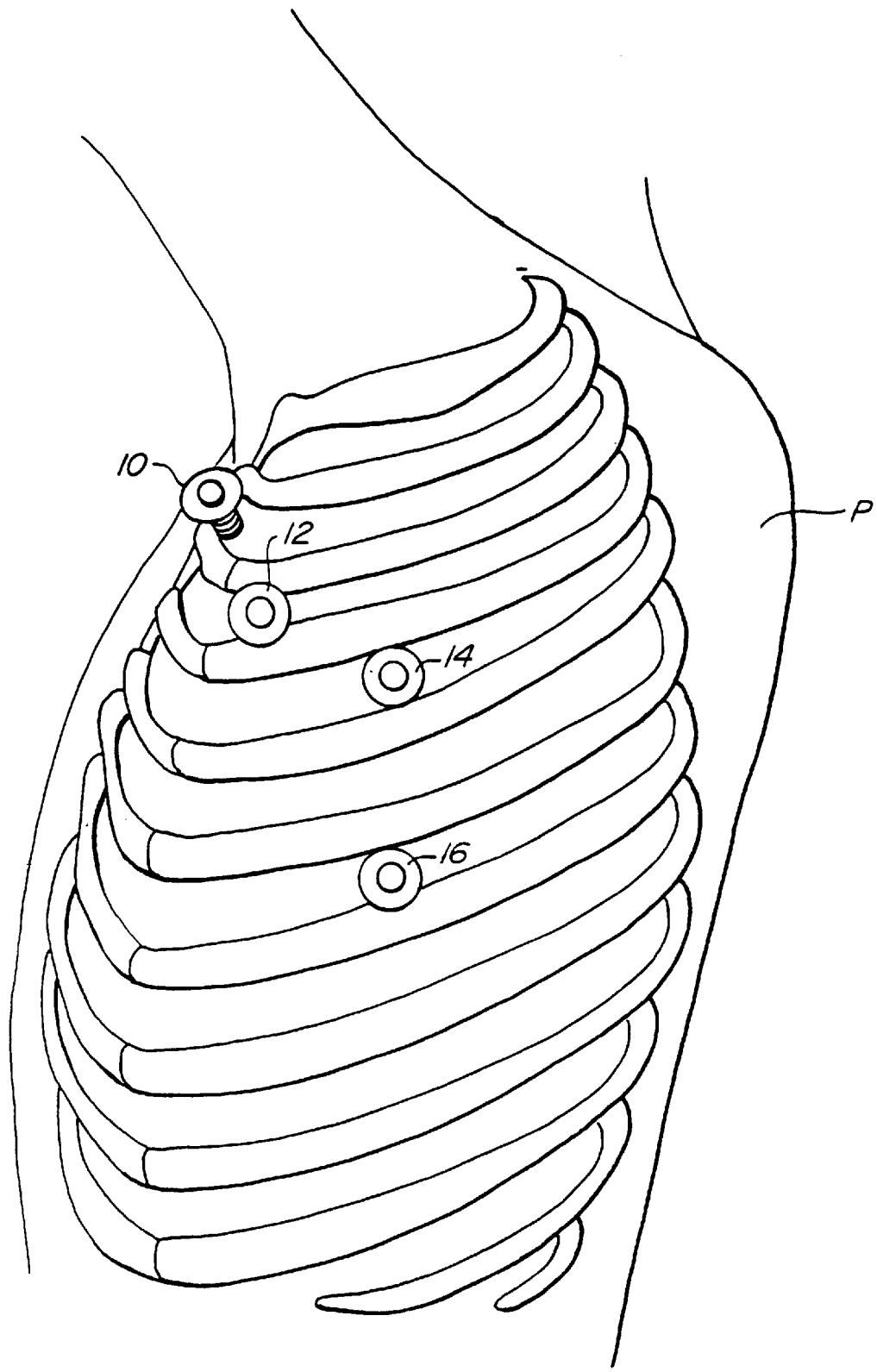
FIG. 1 is a schematic view showing the placement of four trocar sheaths along the lateral chest on the left side of a patient.

After the patient has been prepared as described above, a plurality of access trocar sheaths 10, 12, 14, and 16 will be positioned in the lateral chest of the patient P, as illustrated in FIG. 1. The trocar sheaths of FIG. 1 are shown on the left side of the patient and will be used in the creation of an anastomosis between the patient's left internal mammary artery and the left anterior descending coronary artery, as will be described in detail hereinafter. Note that it will frequently be desirable to have one or more access trocar sheaths in position on the right side of the patient, particularly to permit the introduction of grasping tools to facilitate repositioning the heart, as described in more detail hereinafter. In addition, it may be desirable to position one or more trocar sheaths in parasternal location(s) as well. Usually, one trocar sheath, for example, trocar sheath 12, will be positioned first, and a thoracoscope will be introduced therethrough. The remaining trocar sheaths 10, 14, and 16 can then be positioned based on the relative positions of the coronary arteries and other internal body structures which can be viewed after the thoracoscope has been initially placed.

Figure 2:
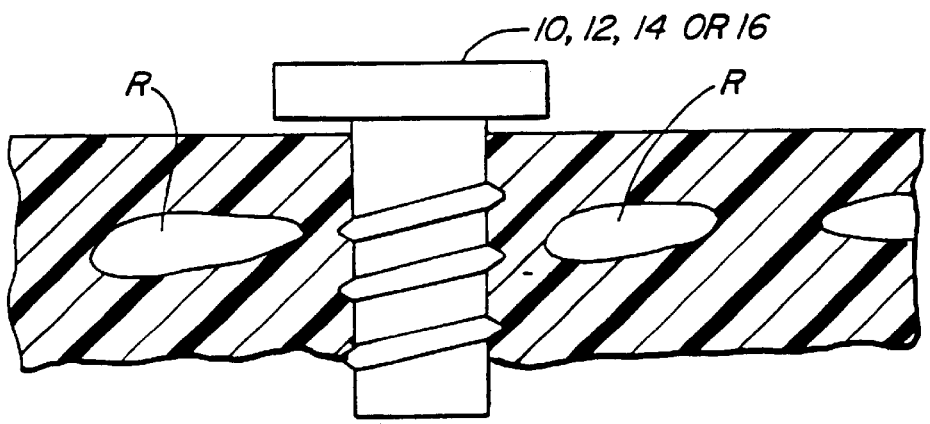
FIG. 2 is a cross-sectional view illustrating the placement of a single trocar sheath between adjacent ribs according to the present invention.

The trocar sheaths 10, 12, 14, and 16 used in the methods of the present invention will generally be shorter than those used for conventional laparoscopic procedures. Typically, trocar sheaths useful for the present invention will have a length in the range from about two to 10 cm, and an internal diameter in the range from two to 15 mm. In addition, the trocar sheaths can be flexible to permit manipulation of tools introduced therethrough. As illustrated in FIG. 2, the trocar sheaths will generally be introduced between adjacent ribs R and will penetrate with their caudal aspect lying just above the superior rib surfaces. Suitable thoracoscopic trocar sheaths are available from Snowden-Pencer Corp. under the tradename Thora-Port™.

The coronary artery bypass graft procedures of the present invention require that a source of arterial blood be prepared for subsequent bypass connection to the narrowed coronary artery at a location beyond the narrowing. Such arterial blood sources will be primarily of two types. First, existing arteries can be dissected from their natural attachments and transected to provide upstream and downstream free ends.

The upstream free end, which is the arterial blood source, will be secured to the coronary artery at a location distal to the narrowing, thus providing the desired bypass blood flow. Second, artificial arterial shunts may be prepared by attaching a natural or synthetic blood vessel, typically a length obtained from a leg vein, at one end to the proximal ascending aorta and at the other end to the target location on a coronary artery. The use of transected arteries is generally preferable since they tend to remain patent for long periods and require only one anastomosis.

The arterial blood source will preferably be the left or right internal mammary artery. It will also be possible to use the gastroepiploic artery in the abdomen. Access to the gastroepiploic artery can be obtained laparoscopically, with the artery being brought into the thorax from the abdominal cavity via a window through the diaphragm. When necessary, it will be possible to prepare free grafts from the aorta. Such free grafts can be formed from veins or arteries harvested from other locations in a patient's body, or may comprise synthetic graft materials. The free graft may be passed into the thorax through either one of the access trocar sheaths or through the aorta (by punching a hole therethrough). The free grafts thus located will be attached at one end to the proximal ascending aorta (to provide the arterial blood supply) and at the other end to the target location on the coronary artery.

The left internal mammary artery is suitable as an arterial source for target locations on the left anterior descending coronary artery, the diagonal coronary artery, the circumflex artery/obtuse marginal artery, and the ramus intermedius coronary artery. The right internal mammary artery is available for connection to all of the same target locations, as well as the right coronary artery and the posterior descending artery. The gastroepiploic artery and free grafts from the aorta will be available for all target locations.

Figure 3:
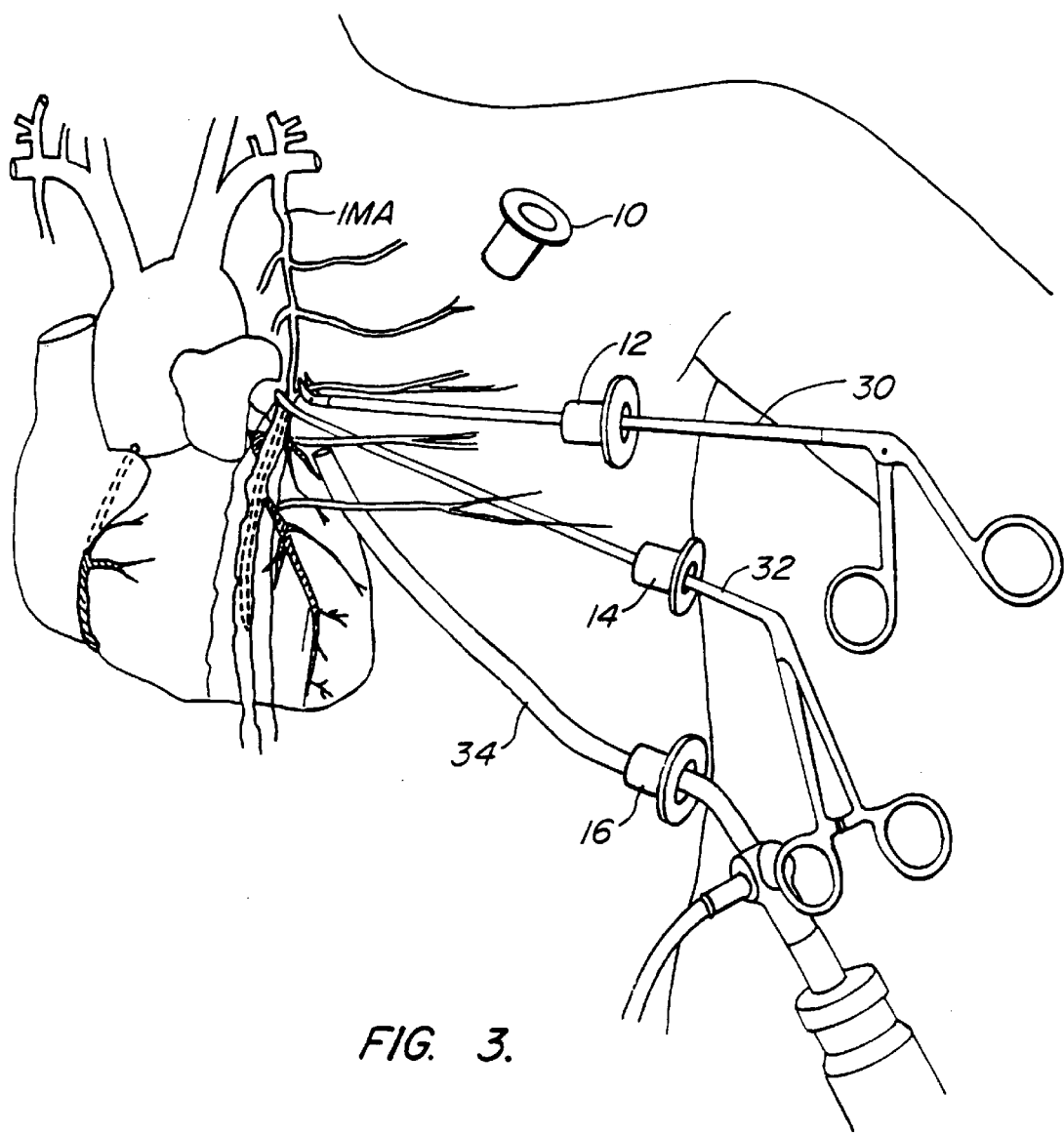
FIG. 3 illustrates the use of an electrosurgical tool introduced through a trocar sheath in order to dissect the left internal mammary artery from the inner thoracic wall to free the artery prior to transection.
Figure 4:
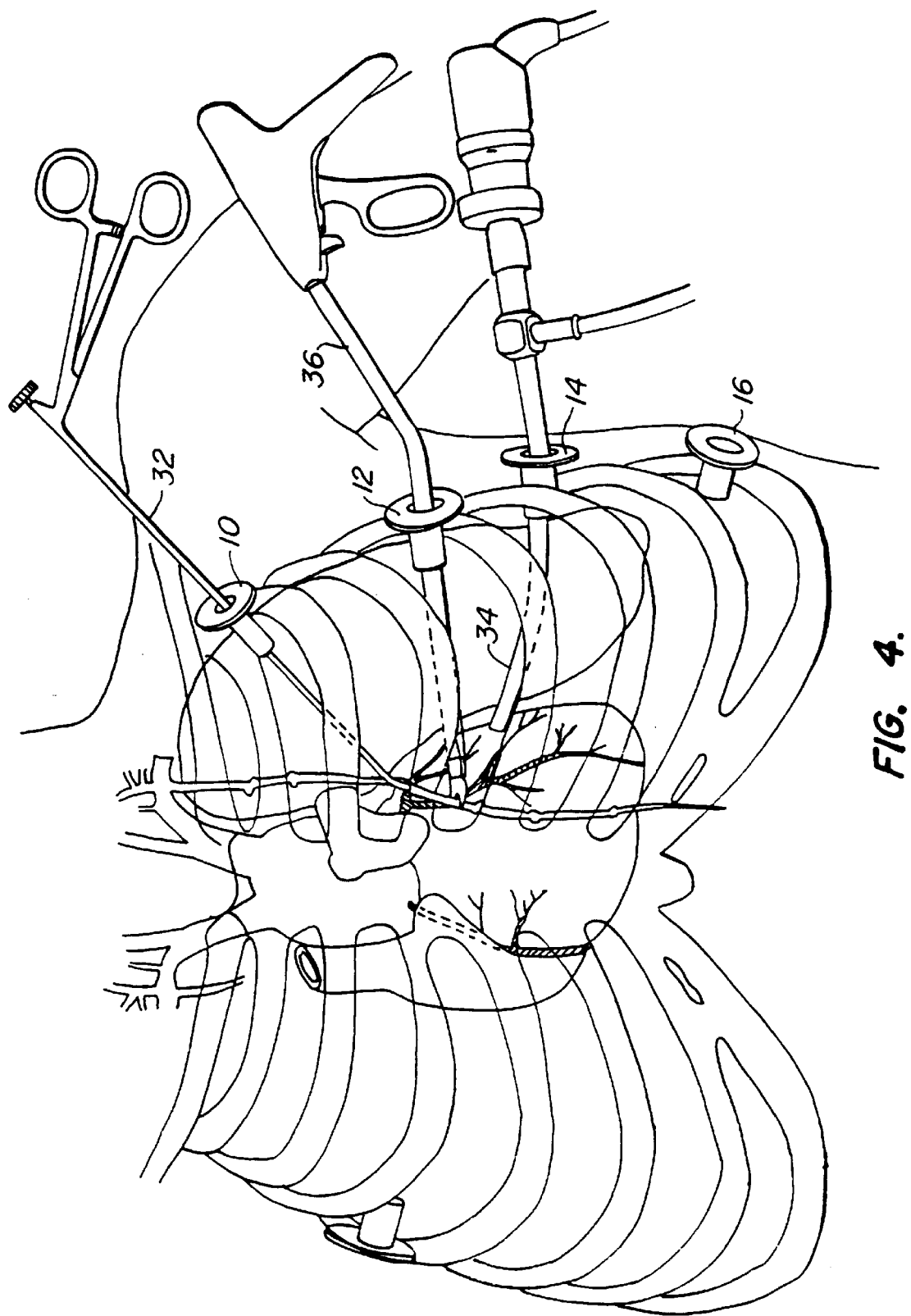
FIG. 4 illustrates the use of a clip applier introduced through a trocar sheath in order to seal off portions of the left internal mammary artery prior to transection.

Referring now to FIGS. 3 and 4, an exemplary procedure according to the present invention for transecting the left internal mammary artery IMA will be described. Initially, the left lung is deflated and an electrosurgical tool 30 is used to dissect a length of the internal mammary artery IMA from the inner thoracic wall. The side branches of the internal mammary artery are sealed. The electrosurgical tool 30 is then introduced through trocar sheath 12 while a grasper 32 or other tool for applying tension on the artery IMA is introduced through trocar sheath 14. The thoracoscope 34 may be positioned through the trocar sheath 16 in order to most advantageously view the operating area at this point in the procedure.

Figure 5:
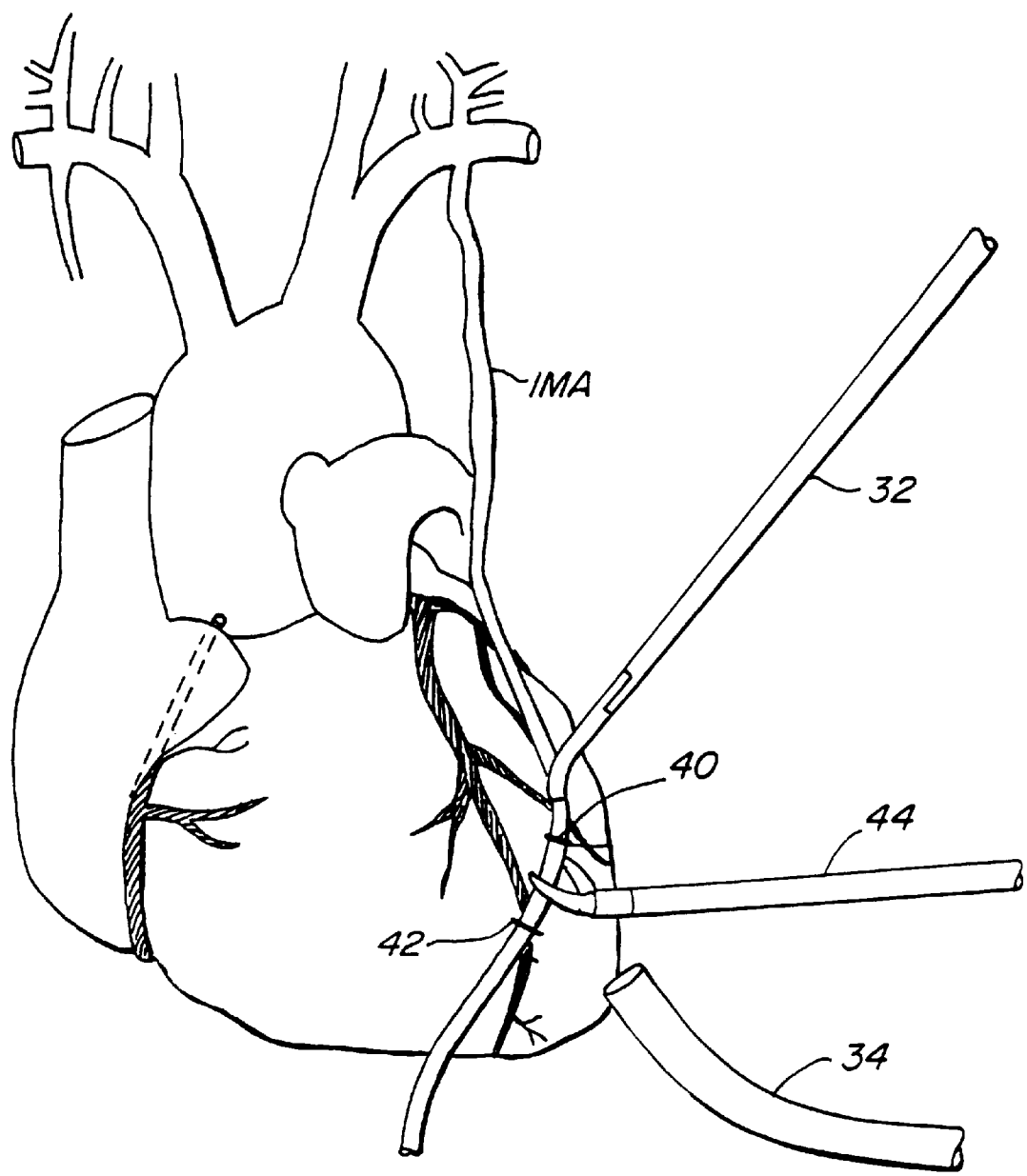
FIG. 5 illustrates transection of the left internal mammary artery to provide an arterial blood source according to the method of the present invention.
Figure 7:
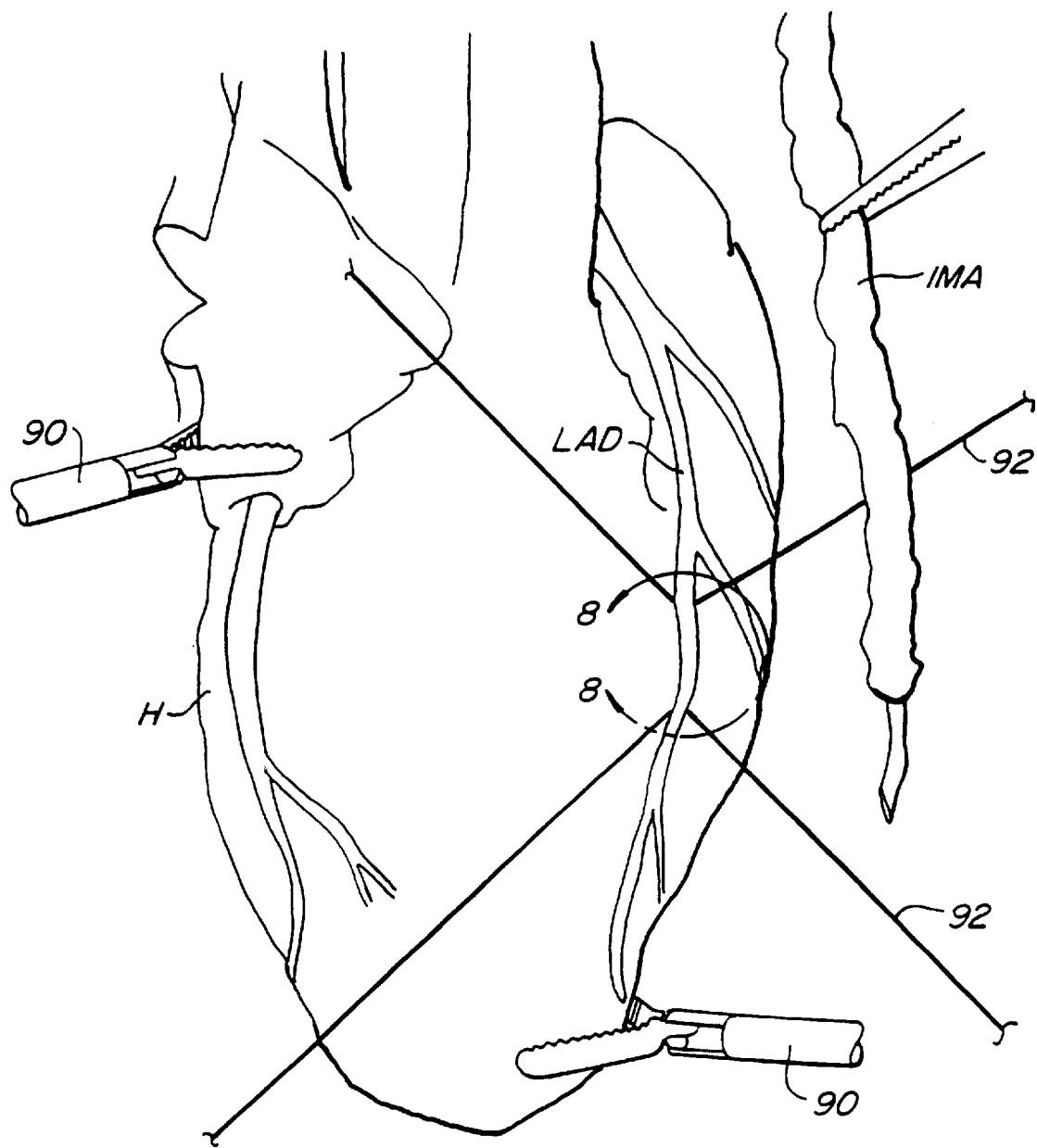
FIG. 7 illustrates the preparation of the heart prior to formation of an arteriotomy in the left anterior descending coronary artery which acts as a target location for connection of the internal mammary artery.
Figure 9:
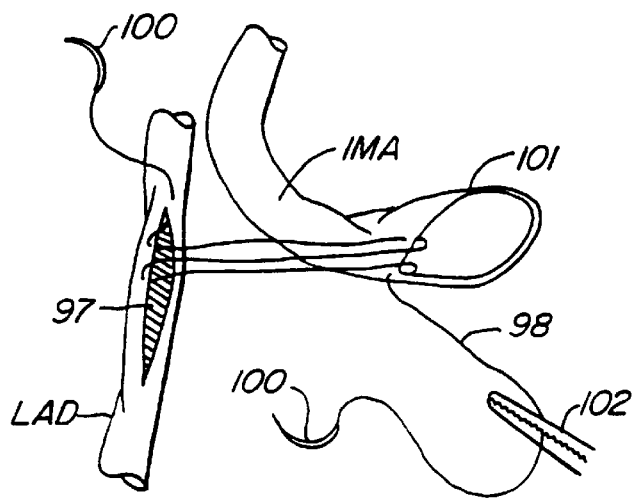
Figure 10:
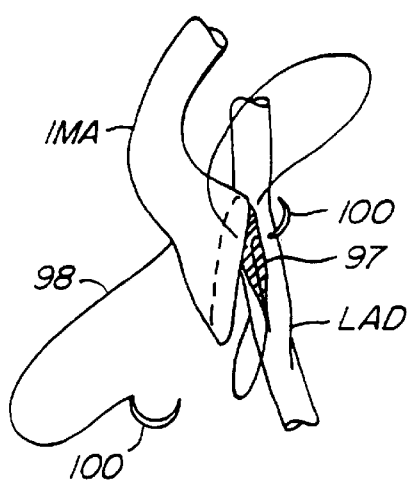
Figure 11:
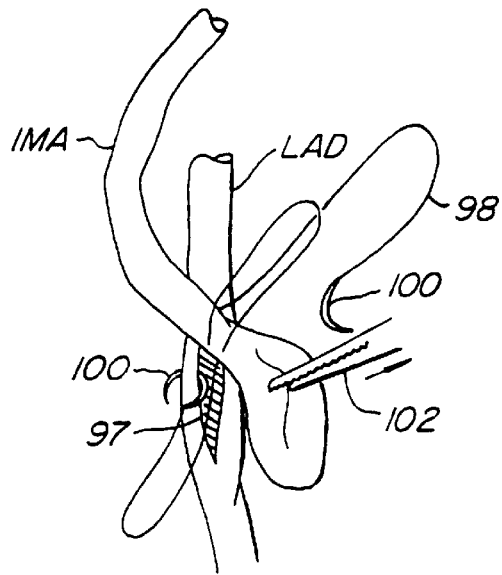
Figure 12:
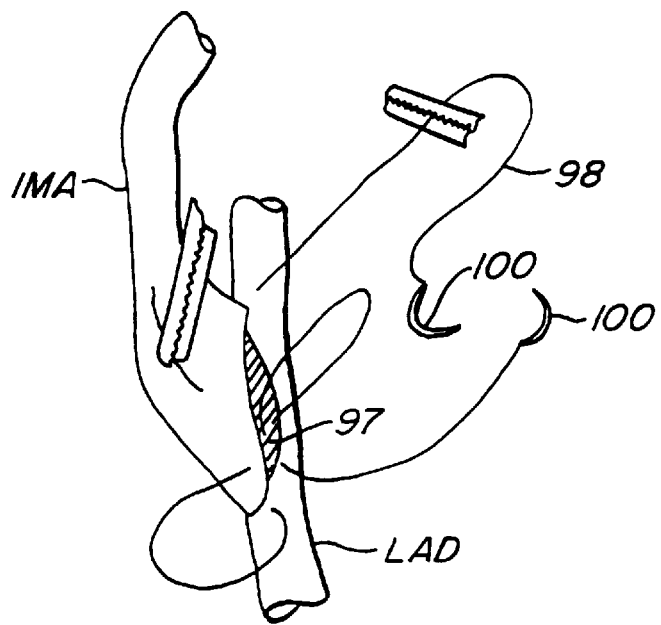
Figure 13:
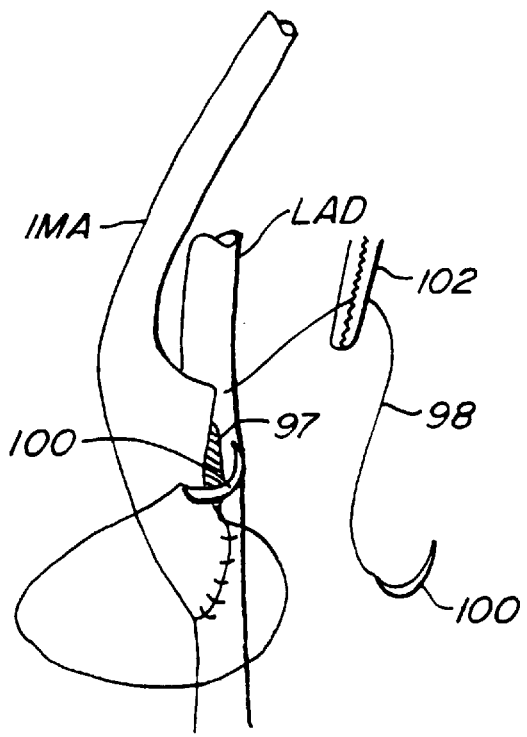

After the internal mammary artery IMA is freed from the thoracic wall, the electrosurgical tool 30 will be replaced with a clip applier 36, with the thoracoscope 34 being moved to trocar sheath 14 and the graspers 32 being moved to trocar sheath 10. The clip applier 36 (FIG. 4) is then used to place one clip 40 upstream and a second clip 42 downstream of a region of the internal mammary artery IMA to be transected, as illustrated in FIG. 5. Upstream clip 40 will be a temporary occlusion device (e.g., a Fogarty clip, Baxter Corp.) which is later removed from the internal mammary artery IMA to establish bypass flow. Downstream clip 42 will be permanently left in place. After the clips 40 and 42 are applied, a cutting tool 44 can be introduced through the same trocar sheath 12 which had received the clip applying tool, and the cutting tool used to cut the artery in a conventional manner. Note that it will be desirable to cut the artery along a diagonal transverse line in order to provide an oval-shaped distal end, as best seen in FIGS. 7 and 9. If necessary, the original cut can be further trimmed to provide a free upstream end suitable for connection to the narrowed coronary artery at a location distal to the narrowed segment. Usually, excess fat will be dissected from the distal 1–2 cm of the severed artery. The dissection can be carried out either within or outside of the thorax, with outside procedures performed by drawing the upstream free end of the artery out through a trocar sheath temporarily.

A particular advantage of the method of the present invention is that both the left and the right internal mammary arteries can be used for bypass in a single procedure. Moreover, each internal mammary artery can be used to form more than one bypass anastomosis including both side-to-side anastomoses and an end-to-side anastomosis. Either internal mammary artery may be used for revascularizations on either side of the heart.

After the internal mammary artery IMA has been transected and prepared, it is necessary to place the patient on cardiopulmonary bypass and to induce cardioplegia (i.e., stop cardiac contraction) prior to connecting the arterial graft to the coronary artery. Cardioplegia can be induced by introducing certain chemicals (usually potassium-containing solutions) into the interior of the myocardium and requires that the patient's arterial system be partitioned to isolate the heart and proximal ascending aorta from the remainder of the patient's vascular system. The isolated heart and ascending aorta can then be selectively exposed to a cold solution that contains a high concentration of cardioplegic chemicals.

Figure 6:
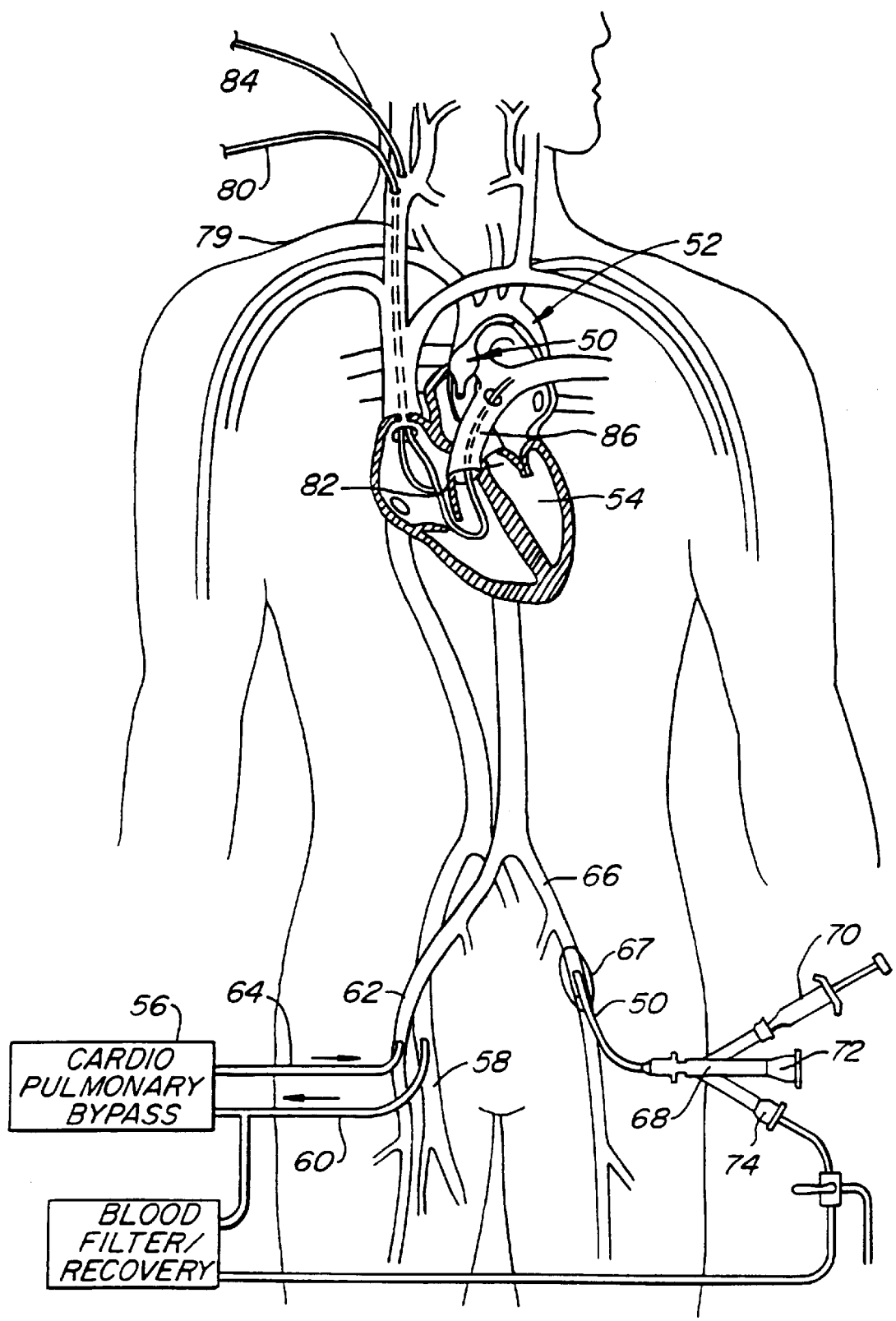
FIG. 6 illustrates the use of an endovascular catheter to partition the patient's heart at a location within the ascending aorta according to the method of the present invention.

Referring to FIG. 6, the arterial system may be partitioned using an aortic occlusion balloon catheter 50 which is positioned in the ascending aorta 52 to separate the left ventricle 54 and proximal portion of the ascending aorta from the rest of the patient's arterial system. A cardiopulmonary bypass system 56 removes venous blood from the femoral vein 58 using a conventional blood withdrawal catheter 60. The bypass system 56 removes carbon dioxide from the blood, oxygenates the blood, and returns the oxygenated blood to the patient's femoral artery 62 through a conventional return catheter 64. The bypass system 56 will operate at a sufficient pressure to drive the circulation of the blood through the patient's arterial system except for that portion which is blocked by the aortic occlusion catheter.

The aortic occlusion catheter 50 is preferably endovascularly introduced over a conventional guidewire to the ascending aorta through the left femoral artery 66 which is entered either percutaneously or through an open cut down 67 of the groin. A proximal hub 68 is located on the proximal end of the occlusion catheter 50 and includes a balloon inflation means, such as syringe 70, a main access port 72 to permit the introduction of instruments, irrigation fluid, and the like. Optionally, a third introduction port 74 may be provided to recirculate a portion of the venous blood from catheter 60. The provision of access ports in the aortic occlusion catheter 50 is optional. It is necessary only that the catheter 50 be able to position a blocking element, such as the inflatable balloon, at the proper location within the ascending aorta. One or more access ports and lumens, however, may be an advantage in a variety of circumstances. For example, the catheter 50 with an access lumen would permit anterograde administration of cardioplegic fluid and would also permit anterograde venting of the left ventricle. Such a lumen could also provide access by acting as an anchored guiding catheter for a variety of other conventional diagnostic and interventional catheters, such as angiography, angioplasty, atherectomy, and similar vascular catheters. The construction of suitable aortic occlusion catheters having such access ports and lumens is described in detail in copending application Ser. No. 071730,559, filed on Jul. 16, 1991, the full disclosure of which is incorporated herein by reference.

As just described, the aortic occlusion balloon catheter 50 will preferably be introduced percutaneously or through an open cutdown of the femoral artery. It may also be possible to introduce the catheter 50 through a trocar sheath placed in the chest, where the catheter is then passed through an aortic arteriotomy in the descending aorta and advanced through the lumen to the location in the ascending aorta, as described above. Introduction via an aortic arteriotomy, however, will generally be less preferred since it is technically more difficult than introduction through the femoral artery. Such introduction, however, may be indicated in cases where the femoral arteries are inaccessible and atherosclerosis of the ascending aorta makes use of an external clamp hazardous (because of possible generation of emboli).

In some cases, the patient's vascular system might be partitioned using an external clamp located on the ascending aorta between the brachiocephalic artery and the coronary ostia. The external clamp would be similar to those employed in open surgical procedures, except that it would be suitable for placement through a trocar sheath under thoracoscopic guidance. Use of an external clamp, however, is generally less preferred since it risks trauma to the aorta, release of emboli from the diseased aortic lumen, and the like.

In addition to provisions for cardiopulmonary bypass and for arterial system partition, the patient will be prepared to receive the introduction of a fluid containing cardioplegic agents to the myocardium. Such agents may be delivered directly into the aortic root and coronary ostia in an anterograde manner employing the aortic occlusion catheter for such delivery. The blocking element of the aortic occlusion catheter prevents escape of cardioplegic fluid into the remainder of the arterial circulation.

Alternatively, the cardioplegic agents can be delivered in a retrograde fashion using a coronary sinus catheter 80 which is introduced in a conventional manner through the patient's right internal jugular vein 79, and includes a balloon at the distal end of the catheter extending into the coronary sinus 82. A pulmonary artery venting catheter 84 may also be introduced through the right internal jugular vein 79 and eventually into the pulmonary trunk 86, as illustrated. The pulmonary venting catheter 84 may include an inflatable balloon (not illustrated) which can be used if necessary to occlude the pulmonary trunk 86 as well as an inner lumen which can vent fluid from the pulmonary trunk and thereby decompress the left ventricle 54 as necessary during the procedure. Use of the aortic occlusion catheter 50, the coronary sinus catheter 80, and the pulmonary venting catheter 84 is described more fully in copending application Ser. No. 07/730,559, the disclosure of which has previously been incorporated herein by reference.

Cardiopulmonary bypass and cardioplegia are then initiated as follows. First, the cardiopulmonary bypass system 56 is activated, followed by inflation of the blocking balloon on the aortic occlusion catheter. The blocking balloon will be positioned between the brachiocephalic artery and the coronary ostia, neither of which will be occluded. In this way, the patient's left ventricle and proximal ascending aorta are isolated from the distal ascending aorta and the remainder of circulation. Cardioplegic fluid may then be perfused, in either an anterograde or retrograde fashion, into the coronary circulation in order to arrest and cool the heart, while the remainder of the arterial system is perfused with blood, coming from the cardiopulmonary bypass system. Preferably, the temperature of the heart will be lowered to as low as 5° C. by perfusing the heart with cold liquid cardioplegic fluid and optionally by topical cooling. Heart temperature may be monitored using a myocardia probe which is introduced either through one of the trocar sheaths or together with one of the coronary catheters. Such topical cooling may be achieved by infusing cold saline over the heart surface within the pericardium or by covering the heart with a cooling jacket, such as a Dailey jacket available from Medtronic, St. Paul, Minn.

After cardiopulmonary bypass has been established, both lungs will be deflated in order to maximize visualization of the cardiac region during the remainder of the method. The left ventricle may be vented, if necessary, using the pulmonary artery vent catheter 84 or an aortic root vent catheter (not illustrated) introduced through an access lumen of the aortic occlusion catheter 50. Alternatively, it may be possible to vent either the pulmonary artery, left atrium, or left ventricle using a catheter passed into the thorax through a trocar sheath, where the catheter is then passed directly through the wall of the artery, atrium, or ventricle. Finally, it is possible to vent the left ventricle using only negative pressure applied to the proximal end of the aortic occlusion catheter, which thus acts as an aortic root vent.

As an alternative to the use of chemical cardioplegic fluids, the patient's heart could be "stopped" for purposes of the present procedures by electrically inducing fibrillation. The necessary electrodes could be introduced through selected trocar sheaths, or could be applied externally on the patient's chest. See, Aikins (1984) J. Thorac. Cardiovasc. Surg. 88:174, for a description of such techniques. Use of chemical cardioplegia to arrest the heart will generally be preferred, since the cooled, arrested heart will have a much lower oxygen requirement than the fibrillating heart, which reduces the likelihood of intraoperative injury to the heart.

The patient is now ready to have the diseased coronary artery or arteries prepared for anastomoses. Initially, a pericardiotomy is performed to provide access to the coronary arteries. The pericardiotomy can be performed using suitable instruments, such as electrosurgical instruments, introduced through the lateral chest trocar sheaths (FIG. 1) while viewing the region through the thoracoscope. The pericardium can be incised and spread open for access, or portions of the pericardium can be excised and removed from the thoracic cavity.

Referring now to FIG. 7, the decompressed heart H will now be repositioned using suitable instruments in order to better expose the coronary artery which is the target for anastomosis. Suitable tools include hooks, suction catheters, grasping rods, pushing rods, and the like. Gravity can also be used to help position the heart if the patient can be turned appropriately. As illustrated in FIG. 7, a pair of graspers 90 may be used to secure opposite sides of the heart and permit turning of the heart as desired. Optionally, additional trocar sheaths may be introduced at other sites of thoracic access. For example, one or more parasternal punctures, one or more punctures in the midclavicular line, and/or a subxyphoid puncture may be introduced.

As illustrated, the left anterior descending coronary artery LAD is first pulled upward from the surface of the heart H and stretched using a pair of elastic members 92 which are introduced through appropriately positioned trocar sheaths. The elastic members 92 place axial tension on the region of the coronary artery LAD which is to be prepared for anastomosis. In addition, they provide a bloodless lumen, permitting excellent visualization.

Figure 8:
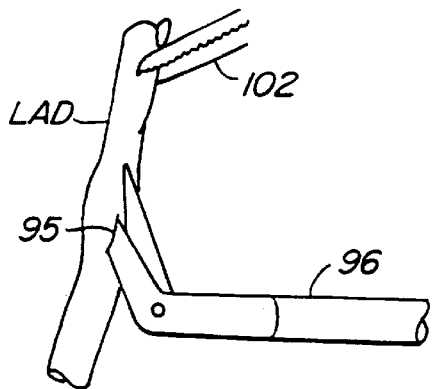
FIGS. 8–13 illustrate the steps of preparing the coronary artery and suturing the internal mammary artery to an incision formed in the coronary artery in order to complete the desired coronary bypass graft. These steps are performed in the region of the coronary artery detailed as circle 8—8 in FIG. 7.

Referring now to FIG. 8, an incision 95 is made in the wall of the coronary artery LAD, where the incision has dimensions selected to match those of the upstream free end of the internal mammary artery graft. The incision 95 is made by first piercing the arterial wall using the tip of a scalpel (not illustrated). Scissors 96 are then introduced through the penetration and used to axially extend the penetration, as illustrated at 97 in FIG. 9.

The internal mammary artery IMA can be joined to the extended incision 97 in the coronary artery LAD by a variety of conventional techniques, including suturing, laser welding, microstapling, and the like. It will be preferred to use conventional suturing techniques as illustrated in FIGS. 9–13. A length of suture 98 has needles 100 at either end, which are manipulated using forceps 102 to join the free upstream end 101 of the internal mammary artery IMA graft to the opening created by the incision 97 in the coronary artery LAD.

Figure 14:
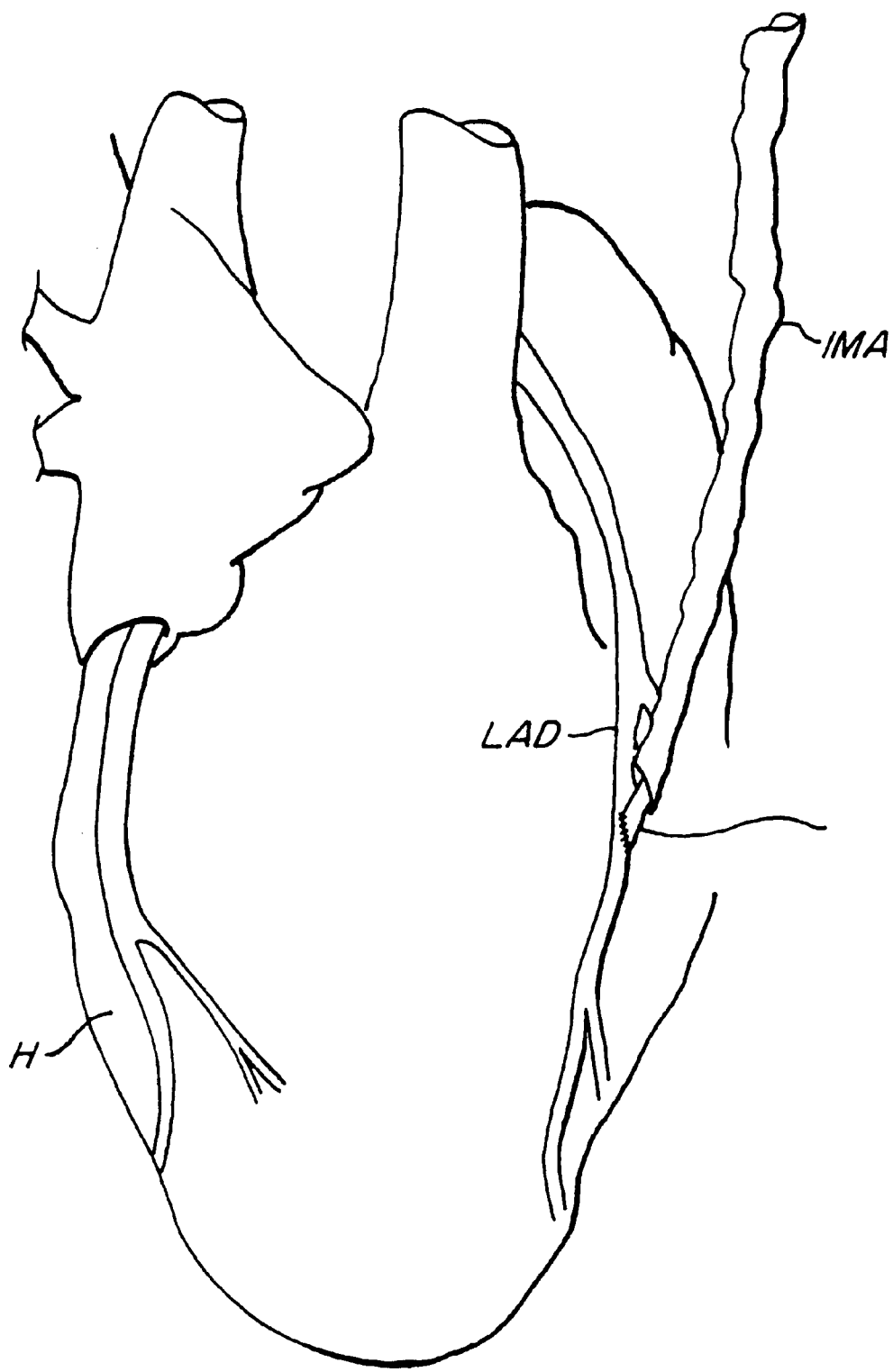
FIG. 14 shows the heart after completion of the coronary artery bypass procedure of the present invention, particularly illustrating the bypass from the left internal mammary artery to the distal left anterior descending coronary artery.

After the suturing is complete, the internal mammary artery IMA will be joined to the coronary artery LAD as illustrated in FIG. 14. The temporary clip 40 will then be removed to permit blood flow from the internal mammary artery IMA into the coronary artery, thus bypassing the previous blockage in the coronary artery. The downstream free end of the internal mammary artery IMA will remain clipped, as described above.

Following completion of the coronary anastomoses, all heart manipulating devices will be removed from the patient, and the heart will be permitted to return to its natural orientation. The aortic occlusion catheter 50 will be deflated. Both lungs will be ventilated, and the coronary arteries will be perfused with blood to initiate cardiac contractions in a conventional manner. If necessary, the heart will be defibrillated to correct its rhythm using electrodes placed either on the heart surface via trocar sheaths or on the patient's body surface. The cardiopulmonary bypass will be gradually reduced and stopped. The aortic occlusion catheter will be removed, and the bypass catheters withdrawn. The groin penetrations will be repaired as necessary, all remaining trocar sheaths will be removed, and all thoracic punctures will be sealed in a conventional manner. Finally, the patient will be recovered from anesthesia.

Although the foregoing invention has been described in some detail by way of illustration and example, for purposes of clarity of understanding, it will be obvious that certain changes and modifications may be practiced within the scope of the appended claims.

What is claimed is:

1. A system for facilitating a closed chest surgical procedure on or around the exterior of a patient's heart comprising:

a scope for viewing the interior of the patient's chest cavity which can be inserted through a small opening in the patient's chest;

means for occluding the patient's ascending aorta at a location between the patient's coronary arteries and the brachiocephalic artery;

a cardiopulmonary bypass system, including means to direct oxygenated blood into the patient's arterial system downstream from the occluded ascending aorta;

means for inducing cardioplegia; and surgical tools for operating on and around the external surface of the heart.

\* \* \* \* \*